United States Patent

Casagrande et al.

[11] 4,029,664
[45] June 14, 1977

[54] PROCESS FOR INTERCONVERSION OF HETEROYOHIMBANE ALKALOIDS

[75] Inventors: Cesare Casagrande, Como; Giorgio Ferrari, Milan, both of Italy

[73] Assignee: Siphar S.A., Lugano, Switzerland

[22] Filed: July 6, 1976

[21] Appl. No.: 702,925

[30] Foreign Application Priority Data

July 7, 1975 Switzerland .................. 8846/75

[52] U.S. Cl. .............................. 260/293.53
[51] Int. Cl.² .............................. C07D 491/14
[58] Field of Search ................... 260/293.53

[56] References Cited

UNITED STATES PATENTS

| | | | |
|---|---|---|---|
| 3,072,664 | 1/1963 | Salkin | 260/294.3 |
| 3,337,561 | 8/1967 | Mueller | 260/294.3 |

*Primary Examiner*—G. Thomas Todd
*Attorney, Agent, or Firm*—Cushman, Darby & Cushman

[57] ABSTRACT

A process is disclosed for the interconversion of alkaloids of the heteroyohimbane group, more particularly of tetrahydroalstonine into raubasine, having the formulae

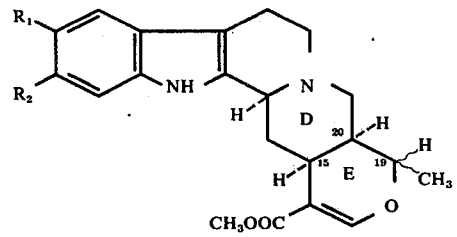

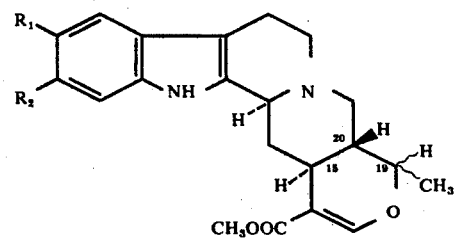

according to which the asymmetry center at C-20 is inverted by several steps involving changes of the ring E structure.

13 Claims, No Drawings

PROCESS FOR INTERCONVERSION OF HETEROYOHIMBANE ALKALOIDS

The present invention relates to a process for the interconversion of alkaloids of the group of the heteroyohimbanes through the inversion of the asymmetry center of C-20 as indicated by the formulae 1 and 2

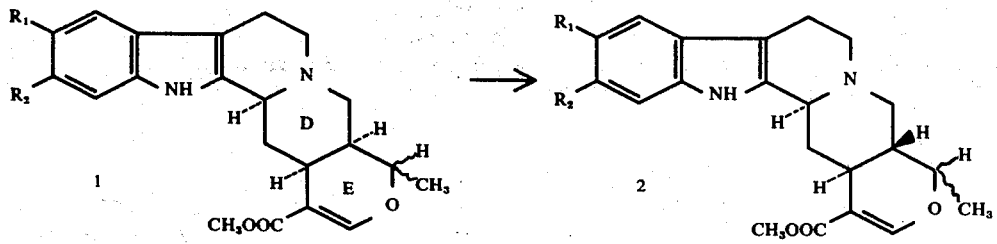

wherein $R_1$ and $R_2$ represent hydrogen atoms or methoxy groups and the sterically undetermined bonds of the substituents at the C-19 atom can indicate both the beta orientation of the hydrogen atom and the alpha orientation of the methyl group, as in the partial formula 3, and, viceversa, the beta orientation of the methyl group and that alpha of the hydrogen atom, as in the partial formula 4.

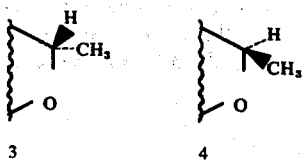

The process, which consists of several steps, is essentially based on the following conversions:

a. opening of the ring E; b) inclusion of the carbon atom C-19 in a carbonyl group, to promote the inversion of the center C-20; c) inversion of the center C-20 with passage to the trans orientation, which is thermodinamically more stable, of the substituents at C-15 and C-20; d) stereospecific reduction of the carbonyl group at C-19, to obtain the desired steric orientation of the substituents at this atom; e) restoration of the ring E.

The process is suitable to obtain alkaloids of the heteroyohimbane of the normal series, such as tetraphylline, raumitorine and rauvanine, and is particularly useful for the conversion of tetrahydroalstonine into raubasine (aymalicine).

In fact the tetrahydroalstonine and the alstonine, the latter being readily converted through reduction into tetrahydroalstonine, are found in good amounts in some plants of the Apocinaceae family, but did not find to date any practical use. On the contrary, an important therapeutical use of the raubasine, is known as vasodilator. The tetrahydroalstonine and the raubasine are respectively represented by the formulae 1 and 2, with $R_1 = R_2 = H$ and with C-19 beta-H and C-19 alpha-$CH_3$.

It has been found that the conversion of the alkaloids of formula 3 into the alkaloids of formula 2 can be suitably carried out as illustrated in the following scheme, the partial formulae of which just represent the part of the molecule (ring E) involved in the conversion.

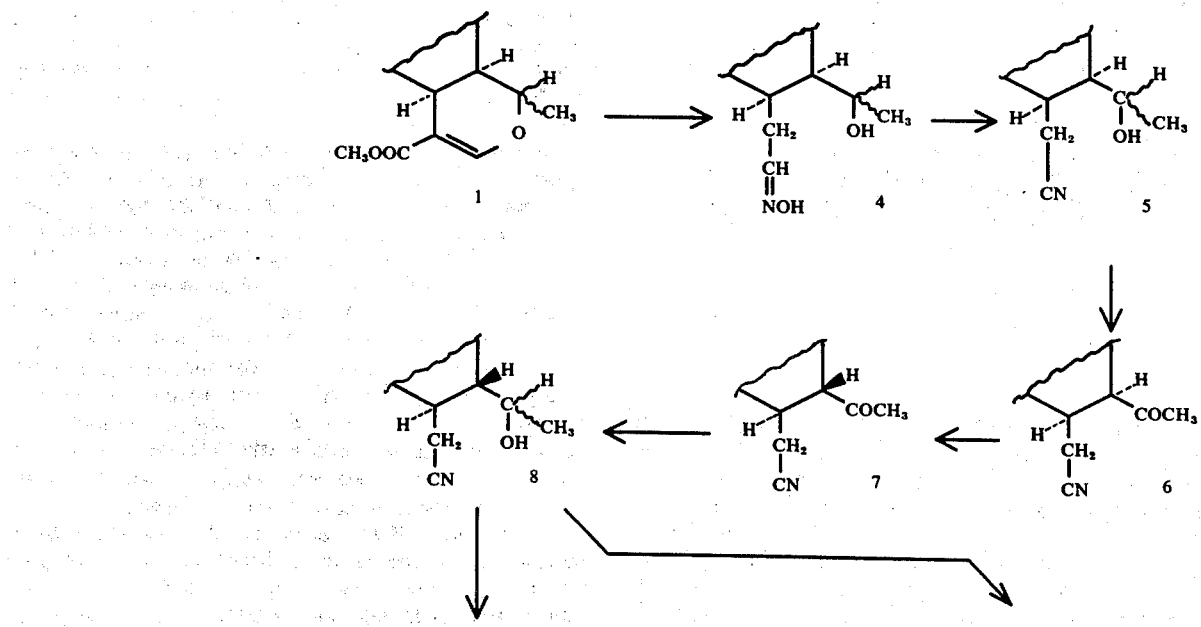

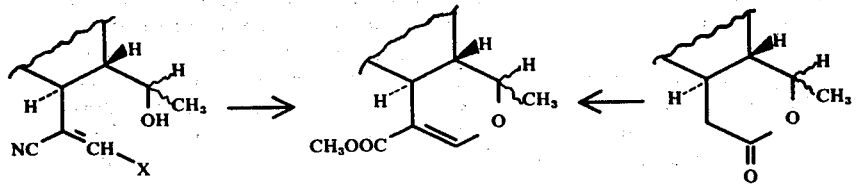

In the formula of the scheme, $R_1$ and $R_2$ and the sterically undetermined bonds of the substituents at C-19 have the above meanings, and X represents an alkoxy group having 1 to 4 carbon atoms or a dialkylamino group the alkyl groups of which comprise 1 to 4 carbon atoms.

By the treatment of an alkaloid of formula 1 with alkali or earth-alkali metal hydoxides in aqueous or alcoholic solution at temperatures of between 20° C and 100° C, such as to induce the saponification of the ester function to a carboxylic group, followed by the heating with mineral acids in aqueous or aqueous-alcoholic solution, at temperatures of between 80° C and 100° C, so as to cause the decarboxylation, and by the further treatment with hydroxylamine of the raw product of the decarboxylation an oxime of formula 4 is obtained; the latter is treated with a reactive derivative (anhydride, chloride, etc.) of an organic acid, such as for instance acetic anhydride, trifluoroacetic anhydride, benzoyl chloride, ethyl chlorocarbonate, phenyl chlorocarbonate, p-toluen-sulfonyl chloride, cyanuryl chloride, phosphonitryl chloride, or even with other dehydrating agents, such as dicyclohexylurea, carbonyl-imidazole, titanium tetrachloride and the like, to obtain a hydroxynitrile of formula 5 (or a derivative thereof, the hydroxyl at C-19 of which has been esterified by the reactant used in the dehydration; such a derivative can be converted again to the desired nitrile of formula 5 by a mild hydrolysis according to the normal techniques of the organic chemistry); the hydroxynitrile of formula 5 is oxidized at a temperature of between −10° C and −30° C with a complex obtained by combining an alkyl sulfide with a halogen or a reactive halogenated derivative, such as for example

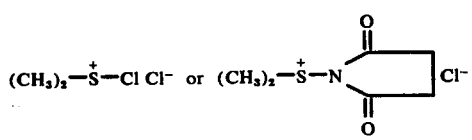

to obtain a ketonitrile of formula 6, which in turn is epimerized to a ketonitrile of formula 7 through the treatment with organic or inorganic strong bases, such as the hydrates and the alcoholates of alkali metals, benzyltrimethylammonium hydrate or 1,5-diazabicyclo [5.4.0]undecene, at temperatures of between 10° C and 100° C; the ketonitrile of formula 7 is reduced in a stereoselective manner to obtain a hydroxynitrile of formula 8, by using a metal hydride, such as for example sodium and boron hydride or the lithium and aluminium hydride, if the steric orientation indicated in the formula 11 is desired, or, viceversa.

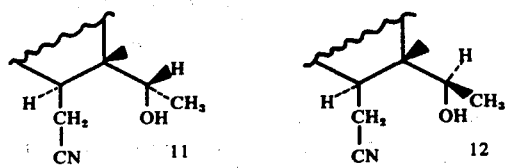

by using hydrogen in the presence of a metal catalyst of the platinum family, such as for instance 10% Pd on carbon, at temperatures of between 20° C and 50° C and under a hydrogen pressure of between 1 and 5 atmospheres, if the steric orientation shown in the formula 12 is desired; the hydroxynitrile of formula 8 is reacted with an orthoformic derivative such as:

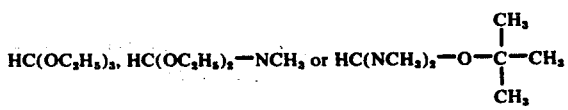

in the presence, if any, of an acid catalyst, to obtain a compound of formula 9; the latter is reacted with methyl alcohol in the presence of anhydrous mineral acids, e.g. hydrochloric acid, to obtain an alkaloid of formula 2.

Alternatively, the hydroxynitrile of formula 8 is converted into the corresponding lactone, having formula 10, through the treatment with alkali hydrates in aqueous or alcoholic solution, at a temperature of between 70° C and 100° C, with subsequent acification, and the resulting lactone of formula 10 is converted into the alkaloid of formula 2 through the condensation with an alkyl formate (having 1 to 4 carbon atoms in the alkyl group) in an inert solvent in the presence of a basic catalyst, such as potassium tertbutylate, sodium triphenylmethyl, sodium hydride, sodium amide, with subsequent reaction with methyl alcohol in the presence of anhydrous mineral acids. As already mentioned, an important embodiment of the invention is the conversion of the tetrahydroalstonine into raubasine, which is carried out as hereinafter described and according to the following scheme, which also represents a preferred embodiment of the present invention.

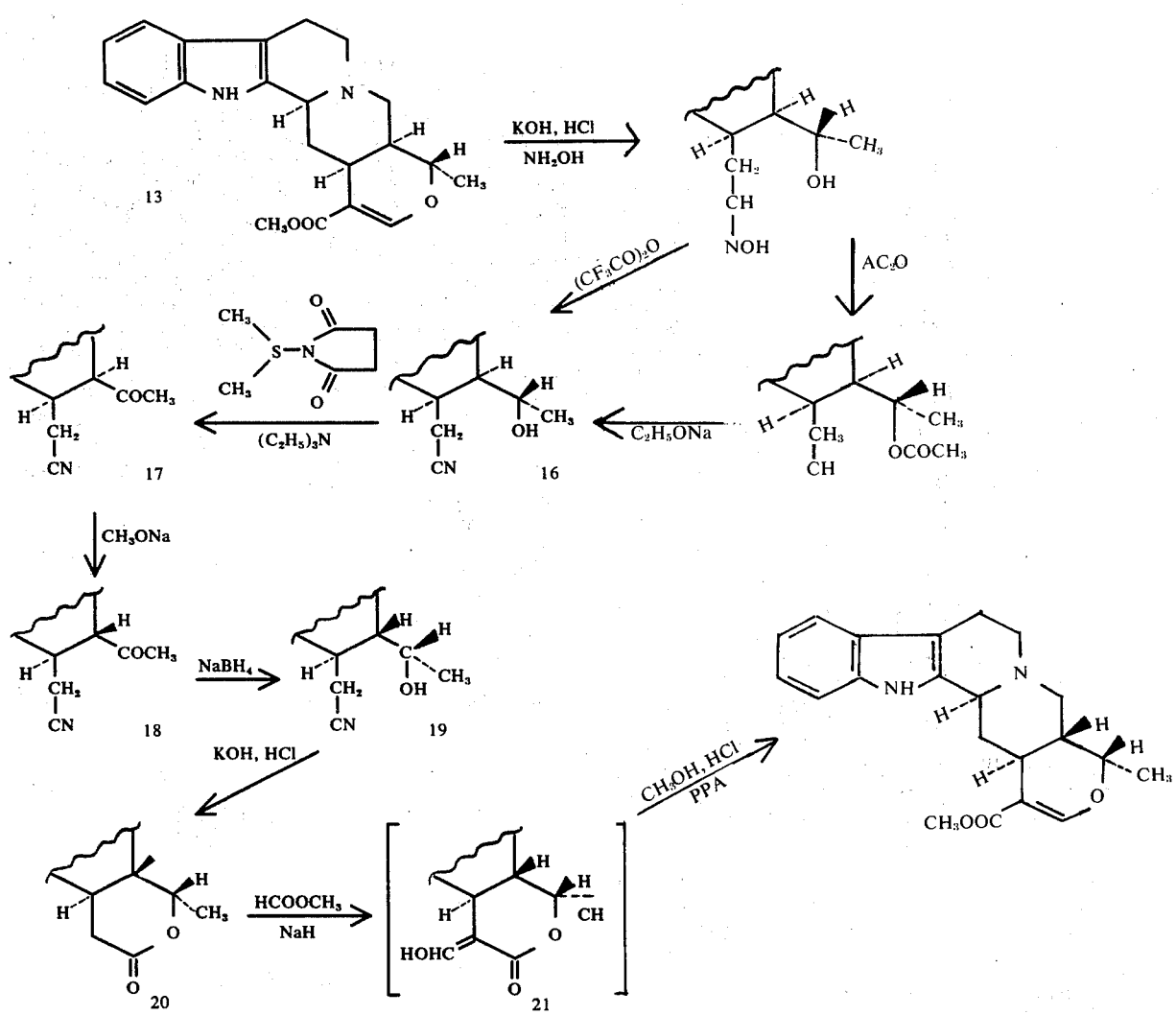

Tetrahydroalstonine 13 is heated with an alcoholic solution of potassium hydrate up to saponification, and then with 2N hydrochloric acid until decarboxylated, and the resulting raw product is converted into the oxime by reaction with hydroxylamine hydrochloride and sodium acetate in boiling alcohol; the oxime 14 is thus obtained with a yield of 90%. The oxime 14 is reacted with acetic anhydride, the acetylnitrile 15 being thus obtained, which is hydrolized to the hydroxynitrile 16 by means of sodium ethylate in alcohol; alternatively, the reaction of the compound 14 with trifluoroacetic anhydride followed by neutralization with aqueous ammonia, gives directly place to the hydroxynitrile 16; the latter is treated at −25° C in chloroform, firstly with the complex formed by dimethylsulfide and N-chlorosuccinimide, and then with triethylamine, the ketonitrile 17 being thus formed, which by means of sodium methylate in methyl alcohol is converted to the epimer 18. The reduction of this compound with sodium borohydride at 15° C in methanol gives place to the hydroxynitrile 19 which, by boiling in alcoholic potassium hydrate and treatment with 2N hydrochloric acid, is converted into the lactone 20. From the lactone, through condensation with ethyl formate in dioxane, the hydroxymethylene derivative 21 is obtained, which is directly converted in the raubasine 22, by treatment with boiling methanol containing anhydrous hydrochloric acid, and then with dioxane containing poliphosphoric acid at 80° C.

EXAMPLE 1

Under atmosphere of inert gas, 200 g. of tetrahydroalstonine and 60 g. of potassium hydrate in 1.5 litres of alcohol are heated to reflux for 4.5 hours: the mixture is neutralized with hydrochloric acid, the methanol is evaporated, the residue is diluted with 7 litres of water and 850 mls of concentrated hydrochloric acid and the mixture is heated to 100° C for 4 hours. After cooling, ammonia is added up to pH 8.5 and the precipitate is recovered, the latter being then heated to reflux for 2 hours in 1.8 litres of alcohol and 0.8 litres of water with 170 g. of hydroxylamine and 360 g. of hydrated sodium acetate. The mixture is diluted with ammonia and water, extracted with chloroform, the extracts are evaporated and the residue is crystallized from methanol. The oxime 14 is thus obtained with a yield of 90%, having melting point of 136–138° C.

EXAMPLE 2

200 g. of the oxime 14 in 2 litres of chloroform are supplemented with 200 mls of trifluoroacetic anhydride; the mixture is maintained at 40° C for 2 hours, then it is diluted with water and neutralized with ammonia. The chloroformic phase is repeatedly washed with diluted sodium hydrate, then treated with anhydrous sodium sulfate and neutral alumina and evaporated. The residue is crystallized from ether;

the hydroxynitrile 16 is thus obtained, having melting point of 197°-199° C.

EXAMPLE 3

100 g. of the oxime 14 are treated with 400 mls of pyridine and 150 mls of acetic anhydride; the mixture is maintained at room temperature for 48 hours and then diluted with water and ice and ammonia is added until pH 8.5. The precipitate is recovered, dried and passed through a column of neutral alumina (activity II of the Brockmann scale) chloroform being used as the eluant. The acetyl-nitrile 15 is thus obtained, having melting point of 232° C (dec.) (from alcohol), which is dissolved in dioxane (750 mls) and treated with the solution of sodium ethylate, as obtained from 1.7 g. of sodium and 75 mls of absolute alcohol. After 3 hours at room temperature, by diluting with water and adding acetic acid until pH 8.5, the hydroxynitrile 16 is obtained having melting point of 197°-199° C (from ether).

EXAMPLE 4

The complex prepared from 42 g. of N-chlorosuccinimide and 23 mls of dimethylsulfide in 750 mls of pure chloroform is added at −25° C with 60 g. of the hydroxynitrile 16, suspended in 300 mls of pure chloroform. The mixture is stirred under inert atmosphere at −25° C for 45 minutes, then 50 mls of triethylamine are added, and the mixture is stirred for 20 minutes and diluted with water. The organic phase is evaporated, diluted with 2N hydrochloric acid and maintained at room temperature for 3 hours. Ammonia is added up to pH 8.5 and the mixture is extracted with chloroform. The extracts are dried over anhydrous sodium sulfate, passed over 300 g. of neutral alumina (activity II of the Brockmann scale) and evaporated, giving place to the ketonitrile 17, having melting point of 157°-159° C (from ether). By eluting the alumina with chloroform containing 2% of methanol, an amount of hydroxynitrile 16 is recovered, which can be again used in the oxidation.

EXAMPLE 5

60 g. of ketonitrile 17 are treated with 600 mls of methanol in which 4.6 g. of sodium were dissolved. After 2 hours at 30° C, the mixture is neutralized with acetic acid and most of the methyl alcohol is evaporated.

The ketonitrile epimer 18 is thus obtained, having melting point of 225°-227° C.

EXAMPLE 6

A suspension of 100 g. of ketonitrile 18 in 2 liters of methanol is treated at 15° C in portions with sodium borohydride; the mixture is stirred for 30 minutes, added with acetic acid up to pH 8, diluted with water and, after evaporation of the methanol, extracted with chloroform. The extracts are dried and evaporated, and the residue is crystallized from ethyl acetate, giving the hydroxynitrile 19, having melting point of 206°-208° C.

EXAMPLE 7

50 g. of hydroxynitrile 19 with 50 g. of potassium hydrate are heated to reflux for 15 hours in atmosphere of inert gas; after evaporation, 1 liter of 2N hydrochloric acid is added and the mixture is maintained at room temperature for 4 hours; thus the hydrochloride of the lactone 20 is obtained, which by addition of water and ammonia gives the corresponding base, having melting point of 265° C (dec.).

EXAMPLE 8

A solution of 300 g. of lactone 20 in 7 liters of dioxane is treated with 65 g. of sodium hydride and, after 30 minutes stirring under inert gas, 200 mls of methyl formate are added. The mixture is kept at room temperature for 24 hours, diluted with water, added with acetic acid up to pH 8, and then most of the solvent is evaporated and an extraction with chloroform is carried out; the extracts are dried and evaporated and the residue, comprising the hydroxymethylene-lactone 21 is heated for 30 minutes with 3 liters of methyl alcohol, containing 5% of anhydrous hydrochloric acid; the methyl alcohol is evaporated and 3 liters of dioxane containing 300 g. of polyphosphoric acid are added, the mixture being then heated to 80° C for 3 hours. Water is then added, and the mixture is made alkaline by sodium carbonate and extracted with chloroform.

The extracts are evaporated and the residue is crystallized from ethyl acetate, the raubasine 22 being thus obtained, having melting point of 247°-249° C, which is identical to the natural substance.

We claim:

1. A process for the interconversion of alkaloids of the group of the heteroyohimbanes having formula

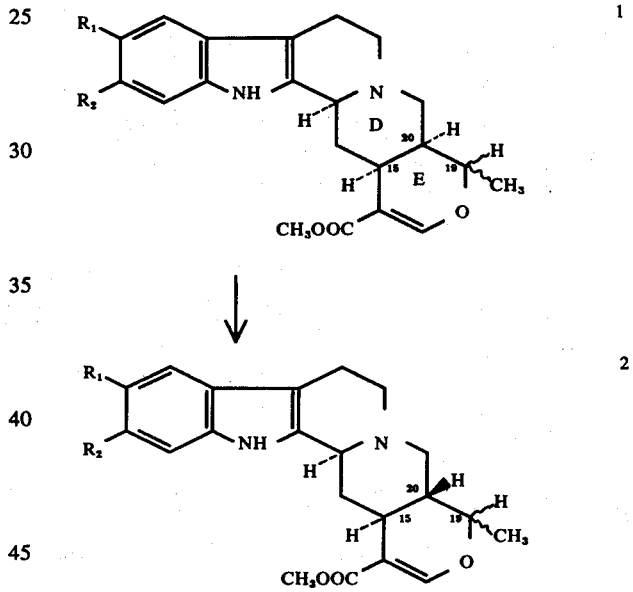

wherein $R_1$ and $R_2$ represent hydrogen or a methoxy group and the substituents at the C-19 atom indicate either the beta orientation of the hydrogen atom and the alpha orientation of the methyl group or viceversa, to obtain corresponding alkaloids having formula

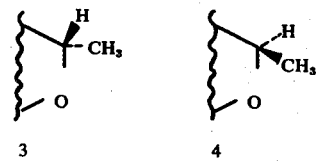

having inverted asymmetry center at C-20, comprising the steps of:
 a. opening of the ring E;
 b. oxidation to a carbonyl group of the carbon atom at C-19;
 c. epimerization with inversion of the center C-20; and d. restoration of the ring E.

2. A process according to the claim 1, wherein, before the step (d), a stereospecific reduction of the carbonyl group at C-19 is carried out to obtain the desired steric orientation of the substituents at the same carbon atom.

3. A process according to the claim 1, wherein the opening of the ring E is effected by: 1) treatment of the starting alkaloid having formula 1 with a hydroxide of an alkali or earth-alkali metal in aqueous or alcoholic solution at a temperature of between 20° C and 100° C; 2) subsequent treatment with a mineral acid in aqueous or aqueous-alcoholic solution at a temperature of between 70° C and 100° C; 3) reaction with hydroxylamine, the oxime of formula 4 being thus obtained.

4. A process according to the claims 1 and 2, wherein, for the step b), the oxime of formula 4 is firstly converted, by reacting with a dehydrating reactant, into the corresponding hydroxynitrile of formula 5, and then the hydroxynitrile is oxidized to the ketonitrile of formula 6.

5. A process according to the claim 4, wherein the dehydrating reactant is selected in the group comprising anhydrides and chlorides of organic acids, particularly acetic anhydride, trifluoroacetic anhydride, ethyl or phenyl chlorocarbonate, p-toluensulfonyl chloride, or dicyclohexylcarbondiimide, carbonyl-imidazole and the like.

6. A process according to the claim 4, wherein the said oxidation is carried out at a temperature of between −30° C and −10° C with the complex resulting from an alkyl sulfide, preferably methyl sulfide, with chlorine or N-chloro-succinimide.

7. A process according to the claims 1 and 2, wherein the epimerization step is effected by treatment of the ketonitrile of formula 6 with an organic or inorganic strong base, preferably, a hydrate or an alcoholate of an alkali metal, or benzyl trimethylammonium hydrate, to obtain the ketonitrile of formula 7.

8. A process according to claim 2, wherein the ketonitrile of formula 7 is reduced to a hydroxynitrile of formula 8, to obtain the steric configuration of the substituents at C-19 according to formula 11, by reaction with metal hydroxide, preferably sodium borohydride.

9. A process according to the claim 2, wherein the ketonitrile of formula 7 is reduced to the hydroxynitrile of formula 8, by hydrogenation in the presence of a metal catalyst of the platinum family, preferably 10% Pd on carbon, to obtain the steric configuration of the substituents at C-19 according to the formula 12.

10. A process according to the claims 8 or 9, wherein the hydroxynitrile of formula 8 is converted to the compound of formula 9, in which X represents an alkoxy or a dialklamino group, the alkyl part containing 1 to 4 carbon atoms, by condensation with an orthoformic derivative, preferably HC (OC$_2$H$_5$)$_3$,

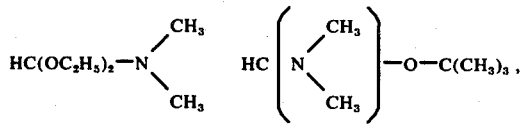

possibly in the presence of an acid catalyst.

11. A process according to the claims 8 or 9, wherein the hydroxynitrile of formula 8 is converted to the corresponding lactone of formula 10 by the treatment with alkali hydrates in aqueous or alcoholic solution at a temperature of 70° C to 100° C and subsequent acidification, and the lactone 10 is condensed with an alkyl formate in an inert solvent, in the presence of a basic catalyst.

12. A process according to the claims 10 or 11, wherein the resulting product is reacted with methyl alcohol in the presence of anhydrous mineral acid, preferably hydrochloric acid, to obtain the desired alkaloid 2.

13. A process according to the claim 1, wherein tetrahydroalstonine is converted into raubasine, according to which tetrahydroalstonine 13 is heated to reflux with an alcoholic solution of potassium hydrate and then with 2N hydrochloric acid, the resulting raw product being then reacted with hydroxylamine hydrochloride and sodium acetate in boiling alcohol giving place to the oxime 14; the oxime 14 is reacted with acetic anhydride to obtain acetylnitrile 15, which is converted into the hydroxynitrile 16 by reacting with sodium ethylate in alcohol, or alternatively by reacting with trifluoroacetic anhydride and subsequent neutralization with aqueous ammonia; the hydroxynitrile is oxidized by treatment at −25° C in chloroform, by firstly reacting with the complex resulting from dimethyl sulfide and N-chlorosuccinimide and then with triethylamine, to obtain the ketonitrile 17; the latter is epimerized by treatment with sodium methylate in methyl alcohol to the keto-nitrile epimer 18, which is reduced with sodium borohydride to the hydroxynitrile 19; the hydroxynitrile is reacted by boiling with alcoholic potassium hydrate, and further acidification with 2N hydrochloric acid to the lactone 20, which in turn is condensed with methyl formate in dioxane in the presence of a basic catalyst and the resulting compound 21 is converted to the raubasine 22 by reacting with boiling methanol containing anhydrous hydrochloric acid and then with dioxane containing polyphosphoric acid at 80° C.

* * * * *